(12) United States Patent
Patel (10) Patent No.: US 6,472,214 B2
(45) Date of Patent: Oct. 29, 2002

(54) FREEZE MONITORING DEVICE

(75) Inventor: Gordhanbhai N. Patel, Middlesex, NJ (US)

(73) Assignee: JP Labs, Inc., Middlesex, NJ (US)

( * ) Notice: Subject to any disclaimer, the term of this patent is extended or adjusted under 35 U.S.C. 154(b) by 0 days.

(21) Appl. No.: 09/897,240

(22) Filed: Jul. 2, 2001

(65) Prior Publication Data

US 2001/0046451 A1 Nov. 29, 2001

Related U.S. Application Data

(63) Continuation-in-part of application No. 09/320,358, filed on May 26, 1999, now abandoned.

(51) Int. Cl.⁷ .............................................. G01N 33/02
(52) U.S. Cl. ............................ 436/2; 436/7; 436/20; 436/164; 436/166; 422/58; 422/61; 426/88
(58) Field of Search ................. 422/56–58; 436/2.7, 436/20, 164, 166; 426/87–88

(56) References Cited

U.S. PATENT DOCUMENTS 3,194,669 A * 7/1965 Koch 4,892,677 A * 1/1990 Preziosi et al. .......... 252/408.1

* cited by examiner

*Primary Examiner*—Lyle A. Alexander
(74) *Attorney, Agent, or Firm*—Joseph T. Guy; Nexsen Pruet Jacobs & Pollard, LLC (57) ABSTRACT

A device composed of (1) a color changing indicator, (2) an optional polymeric binder, preferably having gel forming capability, and (3) an activator solvent system which induces a color change in the indicator when device is frozen, in the region of about 0 to −30° C. An example of the device is an indicator of a fine dispersion of partially polymerized diacetylene of the formula: R—C≡C—C≡C—R, where R is a substituent group, e.g., 4BCMU where R=—(CH$_2$)OCONHCH$_2$COO(CH$_2$)$_4$H, dispersed in a mixture of solvents, e.g., 96:4 water:ED (ethylene glycol diacetate), with or without a polymeric binder. When the temperature of the device is lowered to the freezing point of water, the activator solvent phase separates out of the mixture and induces a color change in the indicator. The device can undergo an irreversible color change, e.g., from blue to red, when the activator mixture is frozen in the region of about 0 to 30° C. The device made from the above system can be used as a freeze indicator for monitoring the undesirable freezing of materials, such as emulsions, latex paints, produce foods, flowers, sea foods, and vaccines which require freeze monitoring.

57 Claims, 3 Drawing Sheets

FREEZE MONITORING DEVICE

PRIORITY APPLICATIONS

This application is a continuation-in-part of U.S. patent application Ser. No. 09/320,358 filed May 26, 1999 now abandoned.

BACKGROUND OF THE INVENTION

1. Field of the Invention

This invention relates to a device for monitoring the freezing temperature history of a perishable product for example, vaccines, fresh produce, flowers, latex paints, emulsions such as milk, fruit juices, and yogurt, to determine if the product has been subjected to a freezing temperature and thus has been damaged.

2. Brief Description of Prior Art

There are a variety of defrost indicators reported in the literature for monitoring of thawing of perishables such as ice-cream. See U.S. Pat. Nos. 4,892,677, 5,685,641, 5,695,284 and 4,735,745, which utilize a diacetylene as an indicator. This type of indicator undergoes a color change when the product temperature undesirably exceeded about 0° C. U.S. Pat. No. 4,892,677, to Preziosi, et al., describes a defrost indicator which is prepared by mixing a diacetylene monomer with a solvent. The mixture is frozen and irradiated in the frozen state to partially polymerize the diacetylene. Once the frozen indicator is exposed to a temperature sufficient to melt the solvent the monomer is extracted from the partially polymerized diacetylene thereby forming a polymer enriched diacetylene phase and a monomer enriched solvent phase. The device of Preziosi et al. is irreversible and unidirectional and only capable of providing a signal with an increase in temperature.

U.S. Pat. Nos. 4,191,125, 5,111,768, and 5,239,942 describe freeze indicators. These indicators usually employ a frangible glass container which contains a colored aqueous solution which ruptures upon freezing and then contacts a wick such as paper upon thawing to indicate that undesirable thawing has occurred. Other representative patents on freeze-thaw type indicators include U.S. Pat. Nos. 4,114,443, 4,145,918 4,148,748, 4,191,125, 5,111,768 and 5,239,942. These type of devices are large, complex, difficult to manufacture, and expensive.

There is a constant need in the art for a device which is simple, easy to make, does not depend upon the use of a frangible glass container, and is economical for commercial production. Especially there is a need for a device to monitor the freeze temperature of such perishable food products as described above, which become damaged and inedible if frozen.

SUMMARY OF THE INVENTION

It is an object of the present invention to provide a device which can indicate temperature excursions below a threshold temperature.

It is another object of the present invention to provide a device which irreversibly indicates a temperature excursion below a threshold temperature which can be easily prepared from readily available, inexpensive materials.

We have discovered that an aqueous solution of certain organic solvents, e.g., ethylene glycol diacetate, will undergo phase separation at the freezing point of water thus concentrating the solvent in liquid form. When the separated solvent then contacts, for example, a partially polymerized diacetylene, it can extract monomer and cause a color change in the diacetylene. Thus, one is aware that the perishable product, e.g., live virus polio vaccine, has been undesirably subjected to a freezing temperature and is possibly damaged.

By this invention there is provided a device comprising: an indicator which is capable of undergoing a color change; and an activator system. The activator system is comprised of a solution of water and an activator solvent. The activator solvent is miscible with water and capable of separating out of the solution at or below the freezing point of water thereby inducing a color change in the indicator upon contact. The indicator is in contact with the activator system and when the device is subjected to a temperature at or below the freezing point of water, sufficient solvent separates from the solution to contact the indicator and induce a color change in the indicator.

Further provided is a process for monitoring the freezing temperature history of an article comprising the step of affixing a device, as described above, to the article and comparing any change in color to a control color.

Furthermore there is provided a color indicator comprising a gel formulation comprised of: water, a water miscible solvent capable of phase separation from the water solution in the temperature range of 0 to −30° C., a gelling agent and a dispersion of a partially polymerized diacetylene.

These and other advantages, as will be realized, are provided in a process for detecting temperature excursions of an article below a threshold temperature. The process comprises the steps of:

a) preparing a freeze indicator comprising an activator system and an indicator.

b) partially polymerizing said indicator at a temperature above the threshold temperature;

c) attaching the freeze indicator to the article wherein when the article is exposed to a temperature below the threshold temperature the activator solvent separates from the water and reacts with the indicator to cause a color change in the indicator. The activator system comprises water and an activator solvent which is miscible in the water above the threshold temperature and separates from the water below said threshold temperature. The indicator is capable of irreversibly reacting with said solvent when separated from said water.

Another embodiment is provided in a method for preparing an indicator for indicating an excursion below a threshold temperature comprising: mixing an indicator with a solvent system wherein the solvent system comprises a host solvent and an activator solvent and wherein the activator solvent is miscible in the host solvent above the threshold temperature and separates from the host solvent below the threshold temperature; exposing the indicator to radiation to polymerize the indicator wherein the exposing is done at a temperature above the threshold temperature; wherein when the indicator is exposed to a temperature below the threshold temperature the activator solvent separates from the host solvent and reacts with the indicator and the indicator changes color.

Yet another embodiment is provided in a method for detecting a temperature excursion of an item below a threshold temperature comprising mixing an indicator with a solvent system wherein the solvent system comprises a host solvent and an activator solvent and wherein the activator solvent is miscible in the host solvent above the threshold temperature and separates from the host solvent below the threshold temperature; exposing the indicator to radiation to polymerize the indicator wherein the exposing is done at a temperature above the threshold temperature; and attaching the indicator to the item wherein when the item is exposed to a temperature below the threshold temperature the activator solvent separates from the host solvent and reacts with the indicator and the indicator undergoes a color change.

A particularly preferred embodiment is provided in a device for detecting excursions below a threshold temperature. The device comprises a compound of the formula R'—C≡C—C≡C—R"; wherein R' and R" are independently selected from $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2, $(CH_2)_b$—CONHR1, $(CH_2)_b$—CO—O—R1, where b=1–10, and R1 is an aliphatic or aromatic radical, and M is a cation, such as $Na^+$ or $(R1)_3N^+$. The device further comprises a solvent system comprising a host solvent and an activator solvent. The activator solvent is miscible in the host solvent above the threshold temperature and separates from the host solvent below the threshold temperature. The compound is exposed to UV radiation above the threshold temperature to partially polymerize the compound. When the device is exposed to a temperature below the threshold temperature the activator solvent separates from the host solvent and dissolves unpolymerized compound thereby causing a color change in the partially polymerized compound.

Yet another embodiment is provided in a device for detecting excursions below a threshold temperature. The device comprises a compound of the formula R'—C≡C—C≡C—R"; wherein R' and R" are independently selected from $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2, $(CH_2)_b$—CONHR1, $(CH_2)_b$—CO—O—R1, where b=1–10, and R1 is an aliphatic or aromatic radical, and M is a cation, such as $Na^+$ or $(R1)_3N^+$. The device further comprises a phase system comprising a host and an activator solvent wherein the activator solvent is miscible in the host above the threshold temperature and separates from the host below the threshold temperature. The device is prepared by the process of exposure to UV radiation above the threshold temperature to polymerize the compound. When the device is exposed to temperature below the threshold temperature the activator solvent separates from the host and dissolves the polymerized compound thereby causing a color change.

Yet another embodiment is provided in a process for detecting temperature excursions of an article below a threshold temperature. The process comprises preparing a freeze indicator with a solvent phase comprising water and ethylene glycol diacetate and a diacetylene phase. The diacetylene phase is partially polymerizing at a temperature above the threshold temperature which will therefore contain monomer and polymer. The partially polymerized diacetylene phase has a first color. The freeze indicator is attached to the article and when the article is exposed to a temperature below the threshold temperature the ethylene glycol diacetate separates from the water in an amount sufficient to extract the monomer from the partially polymerized diacetylene phase thereby forming a monomer depleted diacetylene phase which has a second color.

Yet another embodiment is provided in a device for detecting a temperature excursion below a threshold temperature. The device comprises a diacetylene phase comprising polymerized diacetylene and monomeric diacetylene. The device further comprises a molten solvent phase which comprises a host solvent and an activator solvent wherein the activator solvent is miscible with the host solvent above the threshold temperature and separates from the host solvent below the threshold temperature forming an activator phase. The activator phase dissolves the monomeric diacetylene from the diacetylene phase forming a monomer depleted polymer phase which is a different color from the diacetylene phase.

Yet another embodiment is provided in a device for detecting a temperature excursion below a threshold temperature. The device comprises a diacetylene phase comprising polymerized diacetylene and monomeric diacetylene. The device further comprises a gel phase comprising a gel and an activator solvent wherein the activator solvent is miscible with the gel above the threshold temperature and separates from the gel below the threshold temperature thereby forming an activator phase. The activator phase dissolves the monomeric diacetylene from the diacetylene phase forming a monomer depleted polymer phase which is a different color from the diacetylene phase.

A particularly preferred embodiment is provided in a gel formulation for detecting temperature excursions below a threshold temperature. The gel dispersion comprises water and a solvent which is miscible with water above the threshold temperature and separates from water below the threshold temperature. A gelling agent and dispersion of partially polymerized diacetylene comprising polymerized diacetylene and monomeric diacetylene are provided to the gel formulation. When the gel formulation is exposed to temperatures below the threshold temperature the solvent separates from the water and extracts the monomeric diacetylene from the dispersion and the dispersion changes color.

BRIEF DESCRIPTION OF THE INVENTION AND PREFERRED EMBODIMENTS

The preferred embodiments will be described with reference to the figures wherein similar elements are numbered accordingly.

Figure 1:
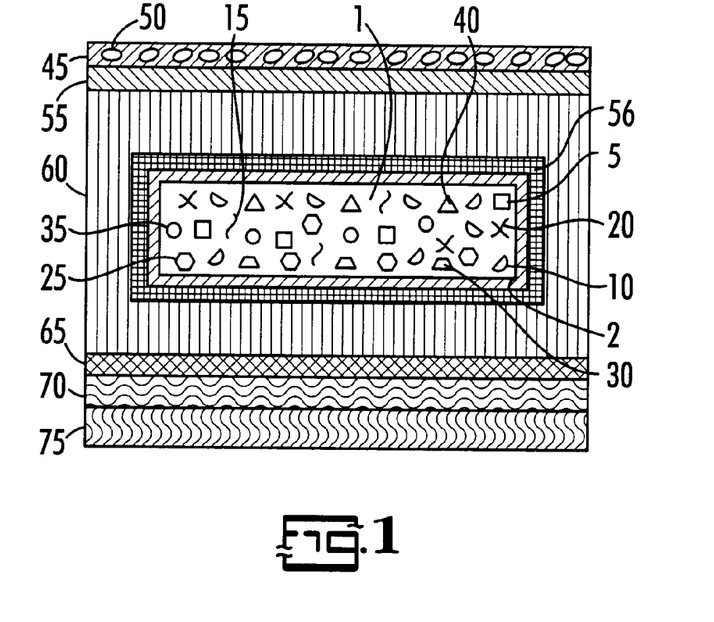
FIG. 1 is a side schematic cross section of one embodiment of the freeze monitoring device of the invention where the activator system is in the form of a gel and the indicator is in the form of a fine crystalline dispersion throughout the gel.

The device can be best described by reference to FIG. 1. As seen in FIG. 1, the device, in its simplest form, is comprised of an activator system, 1, containing a host solvent, 15, preferably water, and an activator solvent, 20. The activator solvent, 20, is miscible with the host solvent above a threshold temperature but separates into a separate phase below the threshold temperature. The activator system is in contact with a freeze indicator 5. The freeze indicator is capable of undergoing a color change in the presence of sufficient concentration of activator solvent, 20, to produce a color change. Above the threshold temperature the activator solvent is not in a sufficient concentration to cause the freeze indicator to change color. As the freeze indicator is exposed to temperatures below the threshold temperature the activator solvent phase separates from the host solvent thereby increasing the concentration of phase separated activator solvent to an amount sufficient to cause the freeze indicator to change color. The activator system, 1, is preferably contained in a compartment, 2, which is formed by the seal, 56, in the plastic container, 60. The freeze indicator, 5, in this embodiment is preferably in the form of a fine dispersion. The activator system, 1, can also include a gelling agent, 25, such that the activator system is a gel, 10. The activator system can also include a binder, 30, which can be gelling or non-gelling, a surfactant, 35, and a nucleating agent, 40, all being present to insure uniform crystallization of host solvent at the freezing point. The container, 60, is preferably sealed by the seal, 56, to encapsulate the contents in the compartment, 2. The top of the device can have a protective coat, 45, which can be scratch resistant and also contain a UV absorber, 50. This protective coat, 45, can be positioned on top of a window film, 55, such that the color change which occurs is readily visible to the observer. The bottom of the device is preferably sealed onto a base film, 65, to which an adhesive layer, 70, can be affixed. The adhesive film allows the device to be affixed to a perishable product where the most widely acceptable utility is expected. To the bottom of the adhesive layer, 70, can preferably be affixed a release film, 75, for ease in packaging and for removal just prior to use. Removal of the preferred release film, 75, enables the entire device to be affixed to a perishable product which is to be monitored for exposure to freezing temperature.

Figure 2:
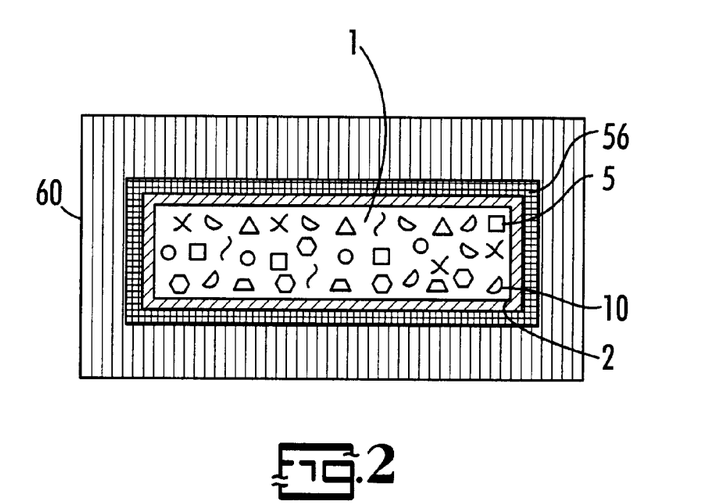
FIG. 2 is a top view of the embodiment of FIG. 1 showing the container, seal and the compartment containing the activator system.

FIG. 2 illustrates the top view of the device of FIG. 1. The protective coat, 45, and window film, 55, are not shown. As illustrated in FIG. 1 the container, 60, and seal, 56, create the compartment, 2, containing the activator system, 1. The activator system, 1, preferably contains all of the ingredients listed in FIG. 1 including the freeze indicator, 5, which is preferably dispersed within a gel, 10.

Figure 3:
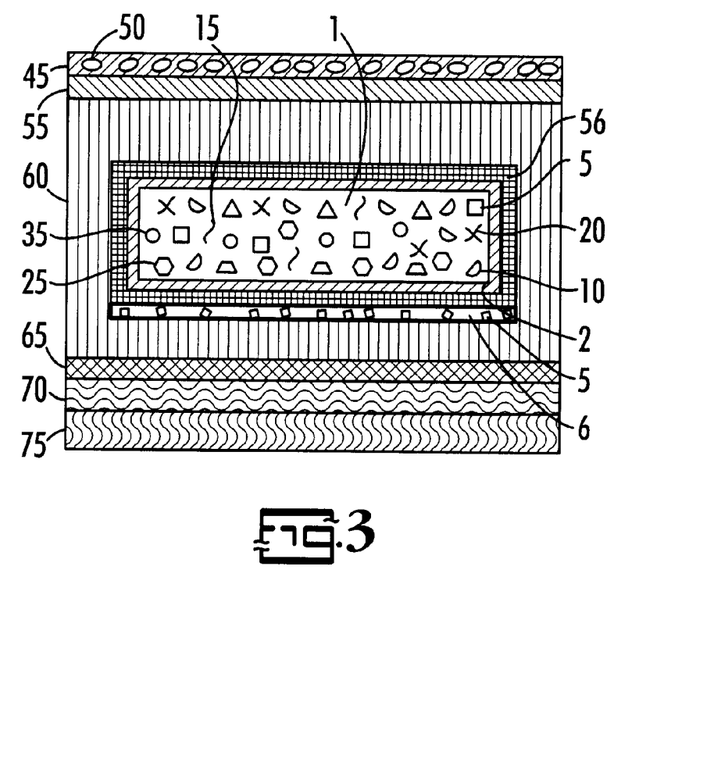
FIG. 3 is a side schematic cross section of another embodiment of a freeze monitoring device wherein the indicator is coated on a substrate below the activator compartment.

FIG. 3 illustrates a side schematic view of another embodiment of the inventive device. The embodiment illustrated in FIG. 3 comprises similar elements to the embodiment illustrated in FIG. 1. In the embodiment illustrated in FIG. 3 the freeze indicator, 5, is inside the compartment, 2, and is coated on a substrate, 6, in contact with the activator system, 1, in the form of a gel, 10.

Figure 4:
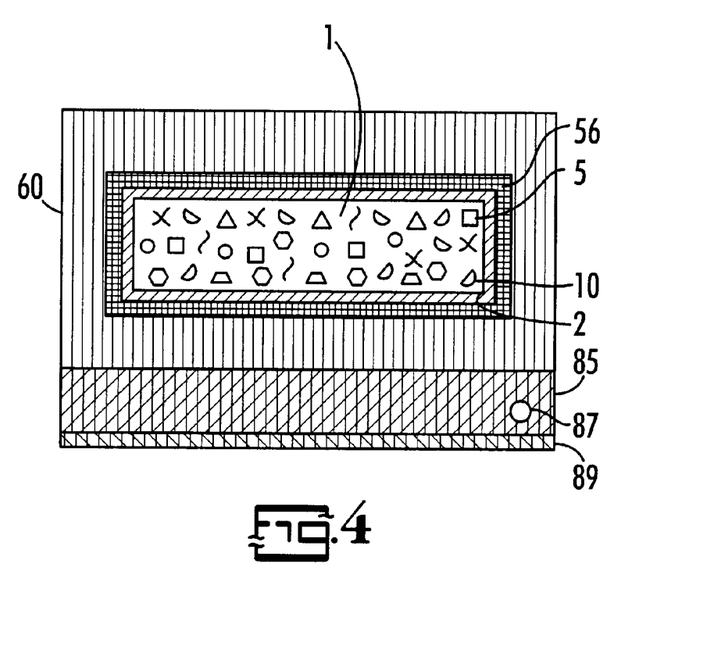
FIG. 4 is a top view of another embodiment of the freeze monitoring device further comprising an additional heat indicator beside the activator compartment to monitor undesirable high temperature history.

FIG. 4 illustrates a further embodiment of the inventive device from a top view. The embodiment illustrated in FIG. 4 further comprises a heat indicator, 85. The heat indicator, 85, is separate from the activator, 1, and has a color indicator, 87, deposited on a substrate, 89, which can be a polyester or plastic backing. The heat indicator can be the same partially polymerized diacetylene used as the freeze indicator, 5, and also as a control indicator to compare against the resulting color of the color indicator, 87. In a particularly preferred embodiment a heat indicator comprises a solid matrix phase and a partially polymerized phase. When the device is exposed to a temperature above the melting point of the solid matrix the monomeric diacetylene is dissolved and the polymerized diacetylene changes color as described in Preziosi et al., U.S. Pat. No. 4,892,677. The combination of a freeze indicator of the present invention, which alerts to a temperature excursion below a lower threshold temperature and a thaw indicator, which alerts to a temperature excursion above an upper threshold temperature, allows for the determination of excursions outside of a preselected temperature band. This is useful for shipping some products, such as shrimp and other sea foods, which spoil above a certain temperature yet lose some flavor if frozen.

Figure 5:
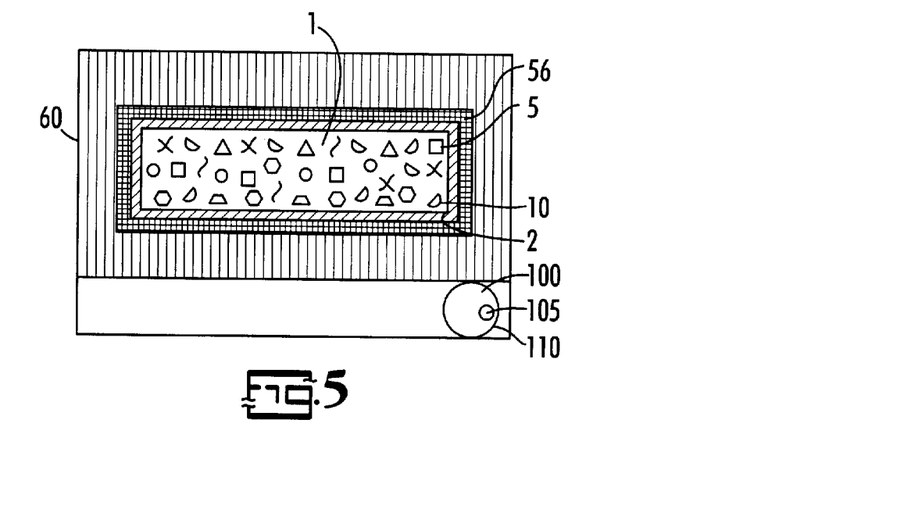
FIG. 5 is a top view of another embodiment of the freeze monitoring device further comprising an additional UV indicator beside the activator compartment to monitor undesirable UV exposure history.

FIG. 5 illustrates a further embodiment of the inventive device from a top view showing the additional presence of a UV indicator, 100. The UV indicator, 100, is separate from the activator, 1, and has a color indicator, 105, deposited on a substrate, 110. The substrate can be a polyester or plastic backing. In a particularly preferred embodiment the color indicator, 105, of the UV indicator, 100, can be the same partially polymerized diacetylene used as the freeze indicator, 5.

Figure 6:
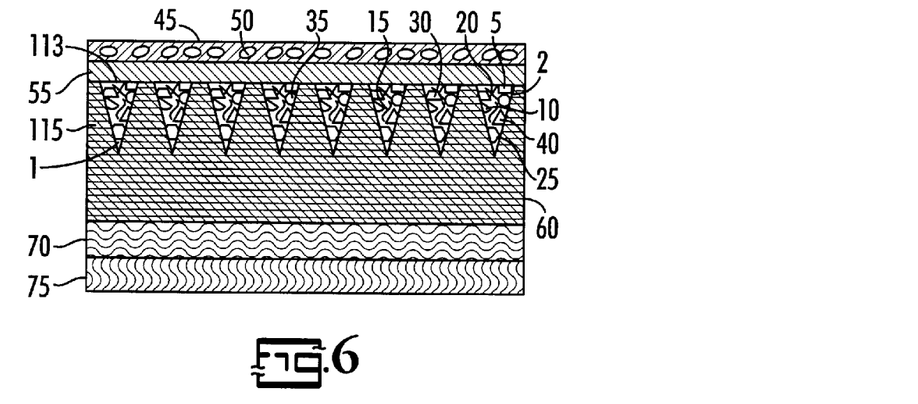
FIG. 6 is a side schematic view of another embodiment of the freeze monitoring device wherein the activator compartment is in the form of a microcup assembly, in which small cups are separately filled with the activator/indicator gel, encased in a container, having a top protective coat and bottom adhesive and release layers.

FIG. 6 illustrates a side schematic view of another embodiment of the inventive device wherein the base film, 115, is in the form of cups, 113, preferably microcups. The base film is preferably a non reactive surface which can be formed, or molded. A particularly preferred base film is an aluminum foil surface. Each microcup, 113, contains a compartment, 2, containing the activator system, 1, as described with reference to FIG. 1 and all of its ingredients in the gel, 10, including: the freeze indicator, 5, host solvent, 15, activator solvent, 20, gelling agent, 25, binder, 30, surfactant, 35, and nucleating agent, 40. An optional, but preferred, protective coat, 45, preferably contains a UV absorber, 50, an adhesive layer, 70 and a release film, 75.

Figure 7:
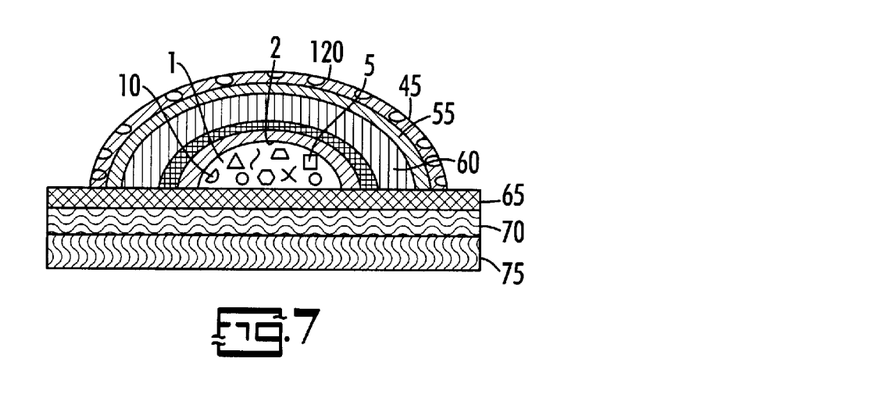
FIG. 7 is a side schematic view of another embodiment of the freeze monitoring device wherein the activator compartment is in the form of a bulb assembly, in which a small bulb is filled with the activator/indicator gel, encased in a container, having a top protective coat and bottom adhesive and release layers.

FIG. 7 illustrates a side schematic view of another embodiment of the inventive device wherein the activator compartment is in the form of a bulb, 120. Each bulb, 120, is a compartment, 2, containing the activator system, 1, preferably as described in reference to FIG. 1 including gel, 10, freeze indicator, 5, host solvent, 15, activator solvent, 20, gelling agent, 25, binder, 30, surfactant, 35, and nucleating agent, 40. An optional, but preferred device, further comprises a protective coat, 45, preferably containing a UV absorber, 50, an adhesive layer, 70, and release film, 75.

While not limited to any theory, the inventive device is based mainly on a combination of two principles which have not previously been combined in this manner. A partially polymerized diacetylene undergoes an irreversible color change when contacted with certain solvents. Also, certain compounds/solvents undergo phase separation or a "salting out effect" from their solution/mixtures when the temperature is lowered to a predetermined temperature, e.g., 0 to −30° C., and preferably 0 to −10° C. For example, when the temperature of a solution of about 20 weight percent or below ethylene glycol diacetate (ED) in water, is lowered to or below 0° C., water freezes and ED phase separates thereby forming a separate liquid phase. If such mixture is in contact with a partially polymerized diacetylene (PPD), such as partially polymerized 4BCMU (pp4BCMU), the unpolymerized monomer molecules become dissolved by ED forming a monomer enriched liquid ED phase. The PPD phase is depleted of monomer thereby causing a color change, e.g., blue-to-red. The chemical formula of 4BCMU is R—C≡C—C≡C—R, where R=[(CH$_2$)$_4$OCONHCH$_2$COO(CH$_2$)$_4$H], and its formal chemical name is 5,12-dodecadiyn-1,12-bis (butoxycarbonylmethylurethane).

One advantage offered by the present invention is the ability to modify the temperature at which the device will change color by the suitable additions of soluble salts to the solvent phase. For example, sodium chloride, calcium chloride, organic salts such as ammonium citrate can depress the freezing point down to −10° C. Similarly, the addition of ethylene glycol can depress the freezing temperature of water down to −30° C. By the proper use and selection of the salt or water soluble organic compounds such as glycol, and weight percentage of solution, the predetermined temperature can be desirably altered and adjusted.

A number of patents have been issued on the use of diacetylenes for applications, such as time temperature indicators for monitoring thermal degradation of perishables, thermochromic materials, recording media, and in radiation dosimeters. Some representative patents on imaging applications using diacetylenes are: U.S. Pat. Nos. 4,412,898; 4,668,598; 4,684,688; 4,705,741; 4,954,428; 4,954,543; 5,139,928; 5,359,200; and 5,420,000. Some representative patents on the use of diacetylenes in time-temperature indicators are: U.S. Pat. Nos. 3,501,302; 3,679,738; 3,723,121; 3,743,505; 3,772,011; 3,772,028; 3,811,895; 3,999,946; 4,066,676; 4,384,980; 4,734,355; 4,784,934, and 4,954,543, which are all incorporated by reference.

Although any material which changes color when contacted with an activator can be used as an indicator, we demonstrated the concept with a partially polymerized diacetylene (PPD) as an indicator.

A large number of partially polymerized diacetylenes which undergo an irreversible color change when contacted with an activator solvent can be used for making the device. Some typical examples of color change of PPDs with solvents are described in a publication by Patel, see J. Macromol. Sci. Phys, B20, 111 (1981). PPDs having the side chain (CH$_2$)$_4$OCONHR1 usually change from blue-to-red when contacted with a solvent such as acetone. Certain PPDs, such as that of "166", having the structure: [R—C≡C—C≡C—R, where R=CH$_2$OCONH(CH$_2$)$_6$H] change from red-to-blue. (See U.S. Pat. No. 5,420,000). Preferred partially polymerized diacetylenes are those which have high solubility in common, nontoxic, high boiling solvents at low temperatures. Esters of diacetylene are a preferred class of indicators as they usually have high solubility in common solvents. Other diacetylenes having functionality such as alkyl, acid, alcohol, urethanes and amides can also be used. The speed of the color change will depend upon parameters such as solubility and particle size of diacetylene, solvent/activator strength, temperature, nature of co-solvent/additive, binder, and nature of the functionality of the diacetylene.

The partially polymerized diacetylene compositions applicable herein are those having the general formula, R'—C≡C—C≡C—R", where R' and R" are the same or different substituent groups. The class of diacetylenes, where R' and R" are the same, is preferred.

Other diacetylenes having the following general formulas can also be used in exemplary devices: higher acetylenes: such as R'—(C≡C)$_n$—R", where n is at least 3 and most preferably n=3–5; split di and higher acetylenes: such as R'—(C≡C)$_m$—Z—(C≡C)$_o$—R", where Z is any diradical, such as —(CH$_2$)$_n$— and —C$_6$H$_4$—, and m and o are separately an integer of 2 or higher; and polymeric di and higher acetylenes: [—A—(C≡C)$_n$—B—]$_x$, where A and B can be the same or different diradical, with exemplary groups including —(CH$_2$)$_n$—, —OCONH—(CH$_2$)$_n$—NHCOO—, and —OCO(CH$_2$)$_n$OCO—. In each example R' and R" can be same or different groups.

Further preferred diacetylenes include those where R' and R" are the same and are selected from: (CH$_2$)$_b$—H; (CH$_2$)$_b$OH; (CH$_2$)$_b$—OCONH—R1; (CH$_2$)$_b$—OCONH—(CH$_2$)—CO—O—R1; (CH$_2$)$_b$—O—CO—R1; (CH$_2$)$_b$—COOH; (CH$_2$)$_b$—COOM; (CH$_2$)$_b$—NH$_2$; (CH$_2$)$_b$—CONHR1; (CH$_2$)$_b$—CO—O—R1; where b=1–10, preferably 1–4, and R1 is an aliphatic or aromatic radical, and M is a cation, such as Na$^+$ or (R1)$_3$N$^+$.

The preferred diacetylenes are the derivatives of 2,4-hexadiyne, 2,4-hexadiyn-1,6-diol, 3,5-octadiyn-1,8-diol, 4,6-decadiyn-1,10-diol, 5,7-dodecadiyn-1,12-diol and diacetylenic fatty acids, such as tricosa-10,12-diynoic acid (TC), pentacosa-10,12-diynoic acid (PC), and cocrystallized mixtures thereof. The most preferred derivatives of the diacetylenes, e.g. 5,7-dodecadiyn-1,12-diol, are the urethane and ester derivatives. Preferred derivatives of 5,7-dodecadiyn-1,12-diol include: urethane (—OCONH—) derivatives, R'(CH$_2$)$_4$—C≡C—C≡C—(CH$_2$)$_4$—R', including: hexyl urethane: R'=OCONH(CH$_2$)$_5$CH$_3$, pentyl urethane: R'=OCONH(CH$_2$)$_4$CH$_3$, butyl urethane: R'=OCONH(CH$_2$)$_3$CH$_3$, ethyl urethane: R'=OCONHCH$_2$CH$_3$, and methyl urethane: R'=OCONHCH$_3$; and ester (—OCO—) derivatives, R'"(CH$_2$)$_4$—C≡C—C≡C—(CH$_2$)$_4$—R'", including: butyl ester: R'"=OCO(CH$_2$)$_3$CH$_3$, ethyl ester: R'"=OCOCH$_2$CH$_3$, and methyl ester: R'"=OCOCH$_3$.

The preferred urethane derivatives can be prepared by reacting 5,7-dodecadiyn-1,12-diol with appropriate isocyanates (e.g. butylisocyanatoacetate) in a solvent, such as tetrahydrofuran, using catalysts, such as di-t-butyltin bis(2-ethylhexanoate) and triethylamine as indicated below:

Catalysts

Preferred ester derivatives can be prepared by reacting 5,7-dodecadiyn-1,12-diol with appropriate acid chlorides in a solvent, such as dichloromethane, using a base, such as pyridine as the catalyst; i.e., Pyridine Several urethane derivatives of (1) 2,4-hexadiyn-1,6-diol, (2) 3,5-octadiyn-1,8-diol, [HO(CH$_2$)$_2$—C≡C—C≡C—(CH$_2$)$_2$OH], (3) 4,6-decadiyn-1,10-diol, [HO(CH$_2$)$_3$—C≡C—C≡C—(CH$_2$)$_3$OH], and (4) 5,12-dodecadiyn-1,12-diol, [HO(CH$_2$)$_4$—C≡C—C≡C—(CH$_2$)$_4$OH], were also prepared and cocrystallized to increase the reactivity of the other diacetylenes.

Though individual diacetylenes can be used, the reactivity of diacetylenes can also be altered by cocrystallization. Cocrystallization can be achieved by dissolving two or more diacetylenes, preferably conjugated, prior to coating. See examples of different co-crystallized diacetylenes by Patel in U.S. Pat. No. 4,189,399.

Diacetylenes develop noticeable color at about 0.1% polymer conversion. Partially polymerized diacetylenes are those having a degree of polymer conversion from 0.1 to 99.9%. A particularly preferred range is 0.5 to 10% conversion. A greater degree of conversion results in a darker blue color and thus a greater dramatic color change and is preferred since a lesser quantity of partially polymerized diacetylene is required to obtain visually observable color change. Fully and completely polymerized diacetylenes can also be used as thin coatings, which change color when contacted with sufficient amount of a suitable solvent.

Though activation with ultra violet light radiation at a wavelength of 254 nm and 60 KeV X-ray are preferable for activation of the device, the devices can also be activated with other high energy radiation such as gamma ray and 10 MeV electrons.

Though we demonstrated the concept with PPDs but one can use any material, e.g., solvatochromic dyes [see Chem. Soc. Reviews 1992, page 1417, Chem Rev. 94, 2319 (1994) and J. Chem Ed. 62, page 460 (1965)] and solvent soluble dyes instead of a PPD. Any other material which can be made to undergo a color change by contacting a phase separated solvent can be used as a solvent activator. An example of a solvatochromic dye is diphenylthiocarbazone in 4 weight percent ethylene glycol diacetate in water which changes from colorless to red when freezing occurs at about 0° C.

A large number of solid and liquid compounds can be used as activators for introducing the color change in indicators such as PPDs. However, a preferred class of activators are solvents which are miscible with water but undergo a phase separation when the temperature reaches the freezing point of water. The preferred activator solvents for PPDs are solvents which dissolve diacetylene monomer at about the freezing point of water. Thus, a preferred solvent will be one which is water soluble and phase separates in the temperature range of 0 to −30° C., and preferably at 0 to −10° C., and dissolves diacetylene monomer at these temperatures. A particularly preferred solvent is ethylene glycol diacetate (ED).

Generally, the activator solvent is present in about 0.05 to 50 weight percent of solution and preferably, from 2-6 weight percent of solution. Solvents having limited (less than 20% by weight) solubility in water are further preferred because they tend to more readily separate out of the aqueous solution at ~0 to −10° C. Also desired characteristics are that the solvent should have a high boiling point and exhibit no diffusion/permeation through the container/film thereby avoiding issues related to contact with solvent or with solvent exiting the containment provided by the device.

Activator solvents useful in the invention device including the following: $C_{1-C15}$ aliphatic, aromatic and substituted aliphatic and aromatic amides preferably acetamide, dimethylformamide and chloroacetamide; alcohols, preferably amyl alcohol, hexyl alcohol, and dichloropropanol; esters, preferably methylpropionate, amylformate, diethyl maleate, ethylene glycol diacetate, ethylsalicylate, and triacetin; nitroalkanes preferably nitropropane; aldehydes, preferably butyraldehyde; carbonates, preferably diethylcarbonate and propylene carbonate; aromatic alcohols/phenols, preferably dihydroxy benzene, benzyl alcohol and phenol; amines, preferably diethanolamine, dimethylpyridine and cyclohexane diamine; ether-esters preferably ethoxyethylacetate, trioxane, tetraethylene glycol dimethylether, benzyl ether, phenylether, propylene glycol ethylether acetate and propylene glycol butylether; alcohol-esters, preferably ethylene glycol monacetate; acids, preferably glutaric acid, isobutyric acid, mandelic acid, and toluene sulfonic acid; ketones, preferably methylethylketone and hydroxyacetophenone; ketone-esters, preferably methylacetoacetate; lactones, preferably propiolactone and butyrolactone and methylpyrrolidone. A particularly preferred example is ethylene glycol diacetate, ED.

A mixture of solvents can also be used as the activator solvent as for example, ethylene glycol diacetate, ED, and ethylene glycol. High boiling polyesters, such as ethylene glycol diacetate, ED, ethylene glycol dipropionate, and the like, are preferred activator solvents. One can use more than one activator solvent in varying proportions. One may use additives such as cosolvents (especially highly polar organic solvents such as alcohols, acids and amines, and ethers) surfactants and nucleating agents. One example of a mixture of activator solvents and surfactant is ethylene glycol diacetate, ED, ethylene glycol and 2-octylphenol.

Since the PPDs do not change color if the mixture of water and activator does not freeze, it is desirable to ensure freezing (ice formation of water) of the cosolvent/mixture by the use of a nucleating agent. A wide variety of nucleating agents are reported in the literature. They include some solid organic and inorganic materials, such as calcium carbonate, sodium chloride, sulfides of copper, tungsten, beryllium and iron, berylium aluminum silicate, silver iodide. A porous material such as paper and cotton can also be used as nucleating agents.

A colorless or a white nucleating agent is preferred. We have found that fine particles such as those obtained by a rapid precipitation of sodium silicate/silica gel and benzoic acid are exemplary for enhancing the freezing process particularly when water is used as the host solvent.

A nucleating agent is particularly preferred when no binder is used. However, we have found that the nucleating agent is not essential if a gel forming binder and a fine dispersion of indicator is used. It appears that the binder/polymer and fine crystals of diacetylene indicator act as nucleating agents by themselves. The results indicate that any inert material in nanometer size (normally known as nano-particles) can be used as a nucleating agent.

In order to make a fine dispersion of indicator in the activator system, it is preferred to use an emulsifying agent such as a wetter/surfactant. A large number of surfactants are available commercially including: polyoxyethylene alkyl phenols, polyoxyethylene esters, polyoxypropylene esters, salts of fatty long chain acids and sulfonates, polyethylene oxides, and polypropylene oxides. Examples are 2-octylphenol, and ammonium laurate.

Although the use of a binder is not absolutely necessary, it is desirable to use a binder to minimize the flow of the solvents/activator in the activator system and container. Any polymeric material which forms a three dimensional network can be used. Both gel forming and non-gel forming materials, such as polymers, can be used as binders. Higher molecular weight binders are preferred. Materials which form a gel in the activator system at room temperature are the most preferred binders. Polymers which are crosslinked or can be crosslinked can also be used. They include natural and synthetic polymers such as gelatin, agar, agarose, "Super Slurper", which is a 60% graft copolymer of starch, polyacrylamide, acrylic acid and sodium salts. The advantage of using Super Slurper (commercially available from the Aldrich Chemical, Milwaukee, Wis.) is that a gel can be formed at room temperature without the necessity of heating followed by cooling to room temperature. One can use a variety of polymers, copolymers and their mixtures as binders to get desired properties such as high gel strength and high gelling temperature.

Inorganic gelling materials can also be used as binders. A wide variety of sol-gel type materials are reported in the literature. In gel form, these materials can also be used as binders. An embodiment of the device using silica gel as a binder is described herein as Example 5.

Water soluble polymers and gums such as alginates, alkyl and hydroxyalkylcellulose, carboxymethylcellulose, carrageenan, guar gum, gum agar, gum gatti, gum karay, gum tragacanth, locust bean gum, pectins, polyacrylamide, polyacrylic acid, polyethylene glycols, polyvinylpyrrolidone, starch and its modified forms, tamarind gum, xanthan gum, gelatins, and polyethyleneimine, their copolymers including graft copolymers and their mixtures, can be used as binders. Water insoluble polymers which form a gel in a combination of solvent and nonsolvent for the diacetylene can also be used for this device. Such polymers are listed in "Polymer Handbook" by A. Hiltner, Third Edison (J. Brandrup and E. H. Immergut Eds), John Wiley and Sons, New York, N.Y. 1989.

Reversible gel forming polymers listed in the following books and reviews can also be used (1) "Reversible Polymeric Gels and Related Systems", Paul S. Russo, ACS Symposium Series #350, Washington, D.C., 1987; (2) L. L. Hench and J. K. West, Chem. Rev., 90, 33 (1990); (3) "Hydrogels" reported by Nagasaki and K. Kataoka, in Chemtech, p23 March 1997; E&E News, Jun. 9, 1997 p26, Encyclopedia of Polymer Science Technology, 7, 783 (1986); and (4) "Reversible Crosslinking", Encyclopedia of Polymer Science Technology, 4, 395, (1986), L. Z. Rogogovina and G. L. Slonimiski, and Russian Chemical Review, 43, 503 (1974).

The total activator system containing components such as activator, indicator, binder, etc. has to be enclosed in a container for use to avoid contact between the device gel contents and perishable product. The container should preferably be transparent so that the color change is readily visible when it occurs. Although vial type glass and plastic containers can be used, a preferred container is a flexible plastic pouch. Such a pouch can be created by joining/sealing the window and the base materials/films as shown in FIG. 1. It is preferred that both the window and base films, as two separate layers, be substantially impermeable to the activator system and its solvent such that none of the pouch contents comes into contact with the perishable product to be monitored. Impermeability to the activator and its solvent can be achieved by selecting the proper polymer, copolymer, graft copolymer and or by coating the film with a barrier coat or laminating with a film which is a thin barrier film. These materials are well known in the art and within the skill of the ordinary practitioner.

Examples of barrier films which can be used are polymer films, which are highly resistant to permeation of the solvents are further preferred materials for the container. They include, including coated and laminated films made from natural and synthetic polymers, copolymers, graft copolymer and their blends, such as polyolefins (polyethylene, polypropylene, and polybutylene), nylons, polyesters (polyvinylacetate and polyethylene terephthalate), polyvinyls (polyvinylchloride, polyvinylidene chloride), polyacrylates, polycarbonates, ionic polymers, cellulose acetate, and regenerated cellulose. Preferred is Saran wrap which is a multilaminated layer of polyvinylidene chloride, polyester and polyethylene.

The base film can be transparent or opaque. One can use metal foil such as aluminum or metallized plastic film, such as with the microcup configuration. For most applications, a transparent barrier plastic film is preferred such as polyester or Al foil.

The basic requirements for the window film are: transparency, to visually witness the color change; and impermeability, to prevent the activator solvent from diffusing out. The window film may optionally have a scratch resistant top coat, such as polyurethane, polystyrene, epoxy or polyester. Preferred film is a coated laminated polyester. Also, the window coat can contain a UV absorber such as hydroxybenzoic acid, benzoic acid and aromatic organic compounds to screen out undesirable UV radiation during the monitoring process.

The device can be made by using any conventional methods, e.g., coating the formulation on a substrate, injecting the formulation into a plastic film compartment, sealing a slice of the gelled formulation and by micro-encapsulation. Coating of activator/solvent diacetylene liquid mixture can be carried out by using any conventional coating method. Also, the activator/indicator/binder formulation can be injected into pre-made compartments, e.g., bulbs or microcups, followed by making each pouch of uniform thickness and then cooling rapidly to room temperature to form a gel.

A preferred composition and method of using the activator/indicator formulation is in the form of a gel in which a gelling agent as described above, is present. Also preferred is the use of a fine dispersion of a diacetylene dispersed throughout the gel. The diacetylene can be made by any of the methods described in U.S. Pat. No. 5,420,000, hereby incorporated by reference for this particular purpose. If the binder is a gel forming material, it will form a gel when cooled to room temperature. The formulation can be made by homogenizing a mixture of a diacetylene, surfactant, binder, activator, and a cosolvent at a high temperature followed by cooling to a lower temperature such as room temperature.

The inventive device can also change color when exposed to additional UV radiation during the monitoring after the diacetylene has been partially polymerized. Thus, visual inspection of the device in which a color change has occurred could present the question as to whether the color change is due to freezing or additional UV radiation. This can be remedied by utilizing on the outside of the device a polyethylene strip of the same partially polymerized diacetylene. If this does not evidence a color change, as compared to the same unexposed starting diacetylene as a control, then one knows that the color change of the actual device is due to freezing and not additional UV radiation.

The time and temperature required for the color change can be varied by varying (1) nature and concentration of indicator diacetylenes, (2) degree of polymerization of diacetylenes, (3) nature and concentration of activator solvent and cosolvent and additives and (4) nature and concentration of binder. By varying the above, the color change can be obtained from 25° C. to −30° C.; from 10 seconds exposure to 1 day exposure below the threshold temperature, and gradual color change to abrupt color change.

The inventive device can also change color at a high temperature, e.g., above 50° C. Thus, visual inspection of the device in which a color change has occurred could present the question as to whether the color change is due to freezing or heating. This can be remedied by utilizing on the outside of the device a polyethylene strip of the same partially polymerized diacetylene. If this does not evidence a color change, as compared to the same unexposed starting diacetylene as a control, then one knows that the color change of the actual device is due to freezing and not heating.

The device offers many major advantages over the other systems reported in the literature. The device changes color only if the solvent system freezes. The device does not change color if the mixture does not freeze. The color change is very dramatic and noticeable in going from blue to red. Other color changes (red-to-blue or red-to-yellow) can also be achieved by selecting proper diacetylenes and solvent systems. The device freezing temperature to be monitored can be altered with additives such as inorganic salts, soluble organic and inorganic compounds, and by altering the concentrations of activator, indicator and binder. Water is used as the preferred solvent and hence the temperature range which can be monitored is about 0 to −30° C. which is the most important range particularly for pharmaceutical formulations and suspensions. Chemicals used in the device are nontoxic. The device is simple and easy to manufacture. The indicator and binder can be designed in a variety of readable forms. The device has a long shelf life. Indicator can also act as a nucleating agent for rapid freezing. The color change can be relatively fast and dramatic. The color change can be seen while the system is still frozen. There is no need to wait for thawing to occur as with other prior art devices which require thawing for a visible color change. Time required for the color change can be varied by degree of partial polymerization, concentration of indicator, activator solvent and binder.

The following Examples are illustrative of carrying out the invention and should not be construed as being limits on the scope and spirit of the instant invention.

EXAMPLES

Example #1
Device without binder

Diacetylene-4BCMU was synthesized according to the procedure reported in the literature (see U.S. Pat. No. 5,420,000). A one weight percent solution of 4BCMU in methylethylketone was coated on polyester film using a #5 wire wound rod. The coating dried within a few minutes. The entire coating was exposed to short wavelength UV light until it turned deep blue wherein the 4BCMU was partially polymerized (pp4BCMU). The film was cut into small strips. About 5 ml each of two and four weight percent solutions of ethylene glycol diacetate (ED) in water were poured into each of ten ml test tubes. The pp4BCMU coated strips were placed into the solutions. One set of tubes was left at room temperature, one set was placed in a refrigerator (~8° C.) and one set was placed in a freezer (~10° C.). The samples stored at room temperature and in the refrigerator did not change color even after a few months. However, those kept in the freezer changed within a few hours. The following solvents were also found to cause a change color with pp4BCMU when mixed with water: dimethyl carbonate, 2-ethoxyethyl acetate, nitromethane, nitroethane (4 drops in 5 ml water) and 1 g of ED in 5 ml of water. The aqueous solution of ED provided much better results from the standpoint of consistency and reproducibility.

Example #2
Indicator with gel forming material as a binder 0.5 Gram of agar was dissolved in a 96:4 w/w solution of 50 ml of hot water:ED respectively. The resulting solution was poured into test tubes and all were cooled to room temperature to form a solid gel. Strips of polyester film coated with pp4BCMU (prepared as per the procedure in Example 1) were inserted into each test tube into the gel and the test tubes were separately placed into the refrigerator and freezer. The strips did not change color in the refrigerator (at 7° C.) while they did change from blue-to-red in the test tubes stored in the freezer (at −7 to −10° C.) within one hour.

Example #3
Fine dispersion of pp4BCMU as an indicator

An emulsion of pp4BCMU was prepared by homogenizing a solution of pp4BCMU in isopropylether with a solution of polyvinylalcohol according to the general procedure described in U.S. Pat. No. 5,420,000. A few hundred grams of the suspension was diluted with 2 liters of water and the resulting fine dispersion of pp4BCMU crystals was allowed to settle. The aqueous layer was decanted and the suspension was filtered and washed with water. The wet suspension was polymerized with UV light to obtain a deep blue color.

The suspension was mixed with a warm solution of agar and "Super Slurper" in water:ED (94:6 w/w) and poured separately into polyethylene and polyester bags. At room temperature, the solution in each of the bags was spread to form a few millimeter thickness layer of a blue gel. The bags were separately placed into the refrigerator and freezer. The blue gel did not change color in the refrigerator (at 7° C.) but did turn red in the freezer (at −7 to −10° C.).

Example #4
Formation of suspension/emulsion of 4BCMU in binders

About 10 mg of pp4BCMU were added to 3 g of a 1% agar and Super Slurper gel in water:ED (94:6 w/w). The contents were heated to about 80° C. and homogenized for a few minutes. The contents became creamy. The creamy contents were cooled with cold water (~15° C.) while still being homogenized. The contents were transferred into plastic bags and each rolled to form a thin layer. The bags were exposed to UV light to polymerize 4BCMU to a deep blue color. The bags were then placed into a refrigerator and a freezer. The blue gel did not change color in the refrigerator (at 7° C.) but did turn red in the freezer (at −7 to −10° C.).

Example 5
Inorganic binder

Silica gel was prepared by neutralizing 10 g. of an 41% aqueous solution of sodium silicate in an aqueous solution of 40 g. of water with 7 g of 12.5% HCl solution under vigorous stirring. The pH was about 7. One gram of ethylene gycol diacetate was added. Strips of polyester coated with pp4BCMU were inserted into the gel and individually stored at room temperature, refrigerator temperature, and freezer temperature. The film changed from blue-to-red in the freezer (at −7 to −10° C.) while the refrigerated (at 7° C.) and room temperature samples were unchanged.

Example 6
Micro-cup device

Micro-cups were created by impressing a strip of aluminum foil with a grooved metal bar. The resulting aluminum strip had a uniform array of small micro indentations of cup shape. The activator/indicator mixture of Example 4 was poured onto the film and the excess wiped off with a doctor's blade. The micro-cups became filled with the formulation. The micro-cup film was laminated with an adhesive tape. The device was exposed to UV light to develop the blue color of pp4BCMU and placed into a freezer at −7° C.). The device changed color within 5 minutes.

Example 7
Monitoring a Vaccine

Microcups would be prepared as in Example 6 with partially polymerized pp4BCMU and affixed to three separate boxes of a vaccine and individually stored at room temperature, refrigerator temperature, and freezer temperature. The film would change from blue-to-red in the freezer (at −7 to −10° C.) while the refrigerated (at 7° C.) and room temperature samples would remain unchanged indicating that the sample stored in the freezer underwent undesirable freezing temperature and may have been damaged.

Example 8
Monitoring a Vaccine

Microcup aluminum foil would be prepared as in Example 6, except that partially polymerized 5,7-dodecadiyn-1,12-diol bis(butylurethane) would be used in place of pp4BCMU. The foil would be affixed to three separate boxes of vaccine and individually stored at room temperature, refrigerator temperature, and freezer temperature. The film would change from blue-to-red in the freezer (at −7° C.) while the refrigerated (at 7° C.) and room temperature samples would remain unchanged indicating that the sample stored in the freezer underwent undesirable freezing temperature and may have been damaged.

Example 9
Freeze Indicator with a Heat Tamper Indicator

An emulsion of 4BCMU was prepared by homogenizing 380 g of 20% polyvinyl alcohol solution in water with 60 g. of 4BCMU in 60 g. of isopropylether at about 55° C. followed by cooling at liquid nitrogen according to the general procedure described in U.S. Pat. No. 5,420,000. To 5 g. of the emulsion of 4BCMU was added 0.5 g. of palmitic acid followed by homogenization for a few minutes. The mixture was coated on a polyester film using a #30 wire wound rod and allowed to dry at room temperature. The coating was exposed to 254 nm UV light until a dark blue color developed. Two small strips (0.5×2 $cm^2$) were cut. These strips are referred to as heat tamper indicators. The heat tamper indicators were mounted onto two freeze indicators of Example 5 using a two-sided adhesive tape. (See FIG. 4). One of these composite devices was placed into the freezer. Only the freeze indicator changed from blue to red within a few minutes while the heat tamper indicator did not change color in the freezer. The other composite devices were heated at different temperatures, e.g., 35, 40, 45, 50, 55, 60 and 65° C. The composite devices did not change color at 45° C. after one day, as compared to a control sample of the same starting diacetylene. Both the freeze and the heat tamper indicators of the composite device started changing color from blue to red within a few minutes at 55° C. At 60° C. and above, they changed color almost instantly. Similar composite devices were made by coating an emulsion of 4BCMU directly onto the freeze indicator surface with equivalent results.

As would be realized the present invention offers advantages over the art including: prior art diacetylene devices are used for monitoring defrosting/thawing of frozen materials. The inventive device monitors freezing of materials such as blood and produce. The present invention records the freezing history which is different from prior art diacetylene devices. The present invention requires that the device be maintained above freezing which is an advantage over the prior art devices which must be maintained below freezing to remain useful. The prior art devices must be activated below freezing, such as by exposure to UV radiation, which is an inconvenience. The present invention changes color in going from a liquid to a solid, or a gel phase to a gel/solution phase while the prior art typically must remain frozen until exposed to temperatures above the activation temperature. As a result the prior art devices can not be shaped to conform to a package or device whereas the present invention can be conformed to any shape since it is in the liquid state. The use of phase separation from a solvent mixture is not described in the art for use with diacetylenes. Prior art devices rely on solvents which melt. The use of a gel is not described in the art for a device since gels do not melt and can not be relied on to dissolve monomer from a partially polymerized diacetylene. The use of gels with diacetylene allows for novel applications and uses.

The present invention has been described with particular emphasis on the preferred embodiments. It would be apparent that alternatives, modifications and alternative embodiments could be prepared without departing from the scope which is set forth in the claims that follow.

I claim:

1. A process for detecting temperature excursions of an article below a threshold temperature comprising:
   preparing a freeze indicator comprising:
      an activator system comprising water and an activator solvent miscible in said water above said threshold temperature and wherein said activator solvent separates from said water below said threshold temperature;
      an indicator capable of irreversibly reacting with said solvent when separated from said water;
   partially polymerizing diacetylene at a temperature above said threshold temperature;
   attaching said freeze indicator to said article wherein when said article is exposed to a temperature below said threshold temperature said activator solvent separates from said water and reacts with said indicator to cause a color change in said indicator.

2. The process of claim 1 wherein said activator solvent is present in the solution of water in about 0.05 to 50 weight percent by weight of solution.

3. The process of claim 1 wherein said activator solvent is selected from a group consisting of: amides, alcohols, esters, nitroalkanes, aldehydes, carbonates, arylalkyl alcohols, phenols, amines, ether-esters, alcohol-esters, acids, ketones, ketone-esters, lactones, and pyrrolidones.

4. The process of claim 3 wherein said activator solvent is selected from a group consisting of: acetamide, dimethylformamide, chloroacetamide, amyl alcohol, hexyl alcohol, dichloropropanol, methylpropionate, amylformate, diethyl maleate, ethylene glycol diacetate, ethylsalicylate, triacetin, nitropropane, butyraldehyde, diethylcarbonate, propylene carbonate, dihydroxy benzene, benzyl alcohol, phenol, diethanolamine, dimethylpyridine, cyclohexane diamine, ethoxyethylacetate, trioxane, tetraethylene glycol dimethylether, benzyl ether, phenylether, propylene glycol ethylether acetate, propylene glycol butylether, ethylene glycol monacetate, ethylene glycol diacetate, glutaric acid, isobutyric acid, mandelic acid, toluene sulfonic acid, methylethylketone, hydroxyacetophenone, propiolactone, butyrolactone and methylpyrrolidone.

5. The process of claim 4 wherein said activator solvent is ethylene glycol diacetate.

6. The process of claim 1 wherein said diacetylene is present as a fine dispersion of crystals in said solvent phase.

7. The process of claim 1 wherein said partially polymerized diacetylene is of the formula: R'—C≡C—C≡C—R", where R' and R" are the same or different substituent groups and are selected from: $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2$, $(CH_2)_b$—CONHR1, $(CH_2)_b$—CO—O—R1, where b=1–10, and R1 is an aliphatic or aromatic radical and M is a cation, such as $Na^+$ or $(R1)_3N^+$.

8. The process of claim 7 wherein b is 1-4.

9. The process of claim 1 wherein said diacetylene is a derivative of one material selected from a group consisting of: 2,4-hexadiyne, 2,4-hexadiyn-1,6-diol, 3,5-octadiyn-1,8-diol, 4,6-decadiyn-1,10-diol, 5,7-dodecadiyn-1,12-diol and diacetylenic fatty acids.

10. The process of claim 9 wherein said diacetylene is selected from a group consisting of a urethane derivative of 5,7-dodecadiyn-1,12-diol and an ester derivative of 5,7-dodecadiyn-1,12-diol.

11. The process of claim 1 wherein said color change occurs at a temperature of about 25 to −30° C.

12. The process of claim 11 wherein said color change occurs at a temperature of about 0 to −10° C.

13. The process of claim 1 wherein said indicator comprises a diacetylene phase comprising a monomeric diacetylene and polymeric diacetylene and wherein when said activator solvent separates from said water said activator solvent extracts said monomeric diacetylene from said diacetylene phase.

14. The process of claim 13 wherein said partially polymerized diacetylene phase comprises about 0.1% to 99.9%, by weight polymer.

15. The process of claim 14 wherein said partially polymerized diacetylene phase comprises about 0.5% to 10%, by weight, polymer.

16. A method for preparing an indicator for indicating an excursion below a threshold temperature comprising:

mixing a diacetylene indicator with a solvent system wherein said solvent system comprises a host solvent and an activator solvent and wherein said activator solvent is miscible in said host solvent above said threshold temperature and separates from said host solvent below said threshold temperature;

exposing said indicator to radiation to polymerize said indicator wherein said exposing is done at a temperature above said threshold temperature;

wherein when said indicator is exposed to a temperature below said threshold temperature said activator solvent separates from said host solvent and reacts with said indicator and said indicator changes color.

17. The method of claim 16 wherein said activator solvent is ethylene glycol diacetate.

18. The method of claim 16 wherein said indicator is a partially polymerized diacetylene.

19. The method of claim 16 wherein said indicator undergoes a color change when exposed to an activation temperature of about 25 to −30° C.

20. A device for detecting excursions below a threshold temperature comprising:

a compound of the formula R1—C≡C—C≡C—R2; wherein R1 and R2 are independently selected from $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2$, $(CH_2)_b$—CONHR1, $(CH_2)_b$—CO—O—R1, where b=1–10, and R1 is an aliphatic or aromatic radical and M is a cation, such as $Na^+$ or $(R1)_3N^+$;

a solvent system comprising a host solvent and an activator solvent wherein said activator solvent is miscible in said host solvent above said threshold temperature and separates from said host solvent below said threshold temperature; and wherein said compound is exposed to UV radiation above said threshold temperature to partially polymerize said compound and wherein when said device is exposed to temperature below said threshold temperature said activator solvent separates from said host solvent and dissolves unpolymerized compound thereby causing a color change in said partially polymerized compound.

21. The device of claim 20 wherein said activator solvent is selected from a group consisting of: amides, alcohols, esters, nitroalkanes, aldehydes, carbonates, arylalkyl alcohols, phenols, amines, ether-esters, alcohol-esters, acids, ketones, ketone-esters, lactones, and pyrrolidones.

22. The device of claim 20 wherein said activator solvent is ethylene glycol diacetate.

23. The device of claim 20 wherein said compound is polymerized from about 0.1% to 99.9%.

24. The device of claim 20 wherein said threshold temperature is about 0 to −10° C.

25. A device for detecting excursions below a threshold temperature comprising:

a compound of the formula R1—C≡C—C≡C—R2; wherein R1 and R2 are independently selected from $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2$, $(CH_2)_b$—CONHR1, $(CH_2)_b$—CO—O—R1, where b=1–10, and R1 is an aliphatic or aromatic radical and M is a cation, such as $Na^+$ or $(R1)_3N^+$;

a phase system comprising a host and an activator solvent wherein said activator solvent is miscible in said host above said threshold temperature and separates from said host below said threshold temperature; and wherein said device is prepared by the process of exposing said device to UV radiation above said threshold temperature to polymerize said compound and wherein when said device is exposed to temperature below said threshold temperature said activator solvent separates from said host and dissolves said polymerized compound thereby causing a color change.

26. The device of claim 25 wherein said phase system is a liquid.

27. The device of claim 25 wherein said phase system is a solid.

28. The device of claim 25 wherein said compound is present as a fine dispersion of crystals in said phase system.

29. The device of claim 25 wherein said compound is present as a film on a support in contact with said phase system.

30. The device of claim 25 further comprising a nucleating agent.

31. The device of claim 25 wherein said threshold temperature is in the region of about 25 to −30° C.

32. A device for detecting a temperature excursion below a threshold temperature comprising:

a diacetylene phase comprising polymerized diacetylene and monomeric diacetylene;

a molten solvent phase comprising a host solvent and an activator solvent wherein said activator solvent is miscible with said host solvent above said threshold temperature and separates from said host solvent below said threshold temperature forming an activator phase; and wherein said activator phase dissolves said monomeric diacetylene from said diacetylene phase forming a monomer depleted polymer phase which is a different color from said diacetylene phase.

33. The device of claim 32 wherein said monomeric diacetylene is a derivative of one material selected from a group consisting of: 2,4-hexadiyne, 2,4-hexadiyn-1,6-diol, 3,5-octadiyn-1,8-diol, 4,6-decadiyn-1,10-diol, 5,7-dodecadiyn-1,12-diol and diacetylenic fatty acids.

34. The device of claim 33 wherein said diacetylene is selected from a group consisting of: R'$(CH_2)_4$—C≡C—C≡C—$(CH_2)_4$—R', where R' is selected from: OCONH$(CH_2)_5$ $CH_3$, OCONH$(CH_2)_4CH_3$, OCONH$(CH_2)_3CH_3$, OCONH$CH_2CH_3$, OCONH$CH_3$, OCO$(CH_2)_3CH_3$, OCO$CH_2CH_3$, OCO$CH_3$.

35. The device of claim 32 further comprising a nucleating agent.

36. The device of claim 32 wherein said activator solvent is 2–6 weight percent of ethylene glycol diacetate, said host solvent is water and said indicator is partially polymerized 5,12-dodecadiyn-1,12-bis(butoxycarbonylmethylurethane) coated on polyester film.

37. The device of claim 32 wherein said device is enclosed in a glass container.

38. The device of claim 32 wherein said device is sandwiched between two layers.

39. The device of claim 38 wherein said layers are impermeable to said activator system.

40. The device of claim 38 wherein one of said layers is a transparent window layer.

41. The device of claim 40 wherein said transparent window film is a coated, laminated polyester.

42. A device for detecting a temperature excursion below a threshold temperature comprising:

a diacetylene phase comprising polymerized diacetylene and monomeric diacetylene;

a gel phase comprising a gel and an activator solvent wherein said activator solvent is miscible with said gel above said threshold temperature and separates from said gel below said threshold temperature forming an activator phase; and wherein said activator phase dissolves said monomeric diacetylene from said diacetylene phase forming a monomer depleted polymer phase which is a different color from said diacetylene phase.

43. The device of claim 42 wherein said activator solvent is selected from a group consisting of: amides, alcohols, esters, nitroalkanes, aldehydes, carbonates, arylalkyl alcohols, phenols, amines, ether-esters, alcohol-esters, acids, ketones, ketone-esters, lactones, and pyrrolidones.

44. The device of claim 42 wherein said monomeric diacetylene is of the formula: R'—C≡C—C≡C—R", where R' and R" are the same or different substituent groups and are selected from: $(CH_2)_b$—H, $(CH_2)_b$OH, $(CH_2)_b$—OCONH—R1, $(CH_2)_b$—O—CO—R1, $(CH_2)_b$—OCONHCH2COO—R1, $(CH_2)_b$—COOH, $(CH_2)_b$—COOM, $(CH_2)_b$—NH_2, $(CH_2)_b$—CONHR1, $(CH_2)_b$—CO—O—R1, where b=1–10, and R1 is an aliphatic or aromatic radical and M is a cation, such as Na$^+$ or (R1)$_3$N$^+$.

45. The device of claim 44 wherein said diacetylene is a derivative of one compound selected from a group consisting of: 2,4-hexadiyne, 2,4-hexadiyn-1,6-diol, 3,5-octadiyn-1,8-diol, 4,6-decadiyn-1,10-diol, 5,7-dodecadiyn-1,12-diol and diacetylenic fatty acids.

46. The device of claim 42 wherein said diacetylene phase is blue and said monomer depleted polymer phase is red.

47. The device of claim 42 wherein said diacetylene phase is present as a fine dispersion of crystals in said gel phase.

48. The device of claim 42 wherein said diacetylene is present as a film on a polymer support in contact with said gel phase.

49. The device of claim 42 wherein said gel phase comprises at least one material chosen from a group consisting of: natural polymer, synthetic polymer, silica gel, gelatin, agar, agarose, and water soluble polymers.

50. The device of claim 42 wherein said gel phase comprises at least one material chosen from a group consisting of: alginates, alkylcellulose, hydroxyalkylcellulose, carboxymethylcellulose, carrageenan, guar gum, gum agar, gum gatti, gum karay, gum tragacanth, locust bean gum, pectins, polyacrylamide, polyacrylic acid, polyethylene glycols, polyvinylpyrrolidone, starch and its modified forms, tamarind gum, xanthan gum, gelatins, and polyethyleneimine.

51. The device of claim 42 wherein further comprising an activator compartment.

52. The device of claim 51 wherein said activator compartment is a series of cups on a surface which are filled with said gel phase.

53. The device of claim 51 wherein said activator compartment is a bulb containing said gel phase.

54. The device of claim 42 wherein said device is enclosed in glass container.

55. The device of claim 42 wherein said device is sandwiched between two layers.

56. A gel formulation for detecting temperature excursions below a threshold temperature comprising:

water;

a solvent which is miscible with water above said threshold temperature and separates from water below said threshold temperature;

a gelling agent; and a dispersion of partially polymerized diacetylene comprising polymerized diacetylene and monomeric diacetylene;

wherein when said gel formulation is exposed to temperatures below said threshold temperature said solvent separates from said water and extracts said monomeric diacetylene from said dispersion and said dispersion changes color.

57. The gel formulation of claim 56 wherein said solvent is ethylene glycol diacetate and said partially polymerized diacetylene is partially polymerized 5,12-dodecadiyn-1,12-bis(butoxycarbonylmethylurethane).

* * * * *